US00PP33028P2

(12) United States Plant Patent
Ammerlaan

(10) Patent No.: US PP33,028 P2
(45) Date of Patent: May 4, 2021

(54) ***ECHEVERIA* PLANT NAMED 'OVPEARLS06'**

(50) Latin Name: *Echeveria lilacina*
Varietal Denomination: OVPEARLS06

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 16/899,837

(22) Filed: Jun. 12, 2020

(30) Foreign Application Priority Data

Nov. 27, 2019 (QZ) ..... PBR 2019/3113

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct variety of *Echeveria* plant named 'OVPEARLS06' which is characterized by a flattened globular prolife with an abundance of foliage held in a basal rosette, dark greyed-green and heavily glaucescent foliage which has a gray appearance, and light pink leaf margins which become white at the apex. The new variety has shown to be uniform and stable in the resulting generations from asexual propagation.

3 Drawing Sheets

Latin name of the genus and species: The Latin name of the genus and species of the novel variety disclosed herein is *Echeveria lilacina.*

Variety denomination: The inventive variety of *Echeveria* disclosed herein has been given the variety denomination 'OVPEARLS06'.

CROSS REFERENCE TO RELATED APPLICATIONS

This application claims priority to the Community Plant Variety Rights application number 2019/3113, filed on Nov. 27, 2019, which is herein incorporated by reference.

BACKGROUND OF THE INVENTION

Parentage: 'OVPEARLS06' is a naturally-occurring, whole-plant mutation of an unnamed *Echeveria lilacina* plant (not patented) which was discovered by the inventor in March of 2009 at a commercial greenhouse in Bleiswijk, the Netherlands. The mutation was noted for its gray foliage with light pink margins.

Asexual Reproduction: Asexual reproduction of the new cultivar 'OVPEARLS06', by way of rooting leaf cuttings, was first initiated in March of 2009 at the inventor's commercial greenhouse in Bleiswijk, the Netherlands. Through eight subsequent generations, the unique features of this cultivar have proven to be stable and true to type.

SUMMARY OF THE INVENTION

The cultivar 'OVPEARLS06' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVPEARLS06'. These characteristics in combination distinguish 'OVPEARLS06' as a new and distinct *Echeveria* cultivar:

1. 'OVPEARLS06' exhibits a flattened globular plant form with foliage arranged in a basal rosette; and
2. 'OVPEARLS06' exhibits spatulate to obovate foliage with an apiculate apex which is held upright near the center of the rosette and becomes progressively more relaxed towards the outer whorls of foliage; and
3. 'OVPEARLS06' exhibits dark greyed-green, strongly glaucescent foliage with a grey general coloration; and
4. 'OVPEARLS06' exhibits foliage with light pink margins which become white at the apex.

BOTANICAL DESCRIPTION OF THE PLANT

Figure 1:
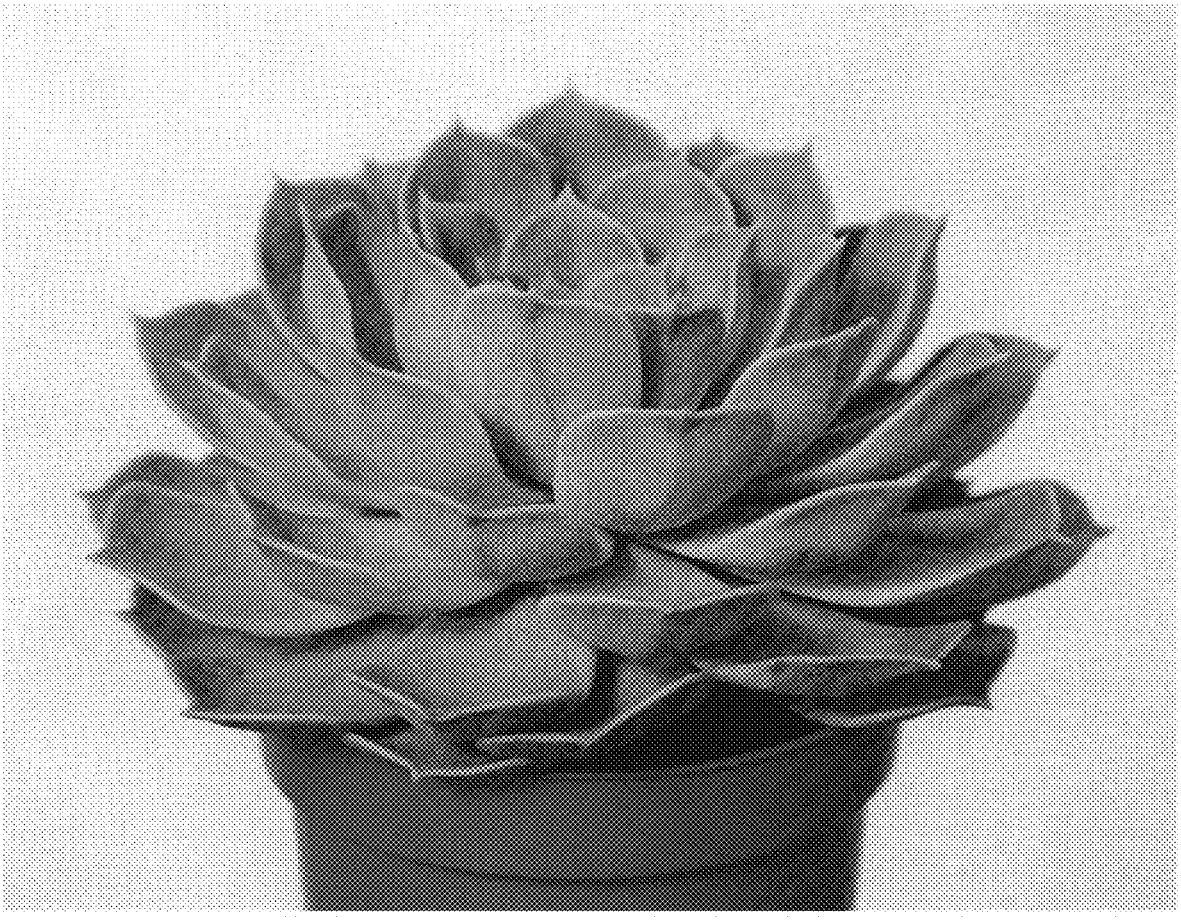
FIG. 1 illustrates, as nearly true as it is reasonably possible to make the same in color photographs of this type, an exemplary plant of 'OVPEARLS06' grown in a commercial greenhouse in Bleiswijk, the Netherlands. This plant is approximately 1 year old, shown planted in a 12 cm container.
Figure 2:
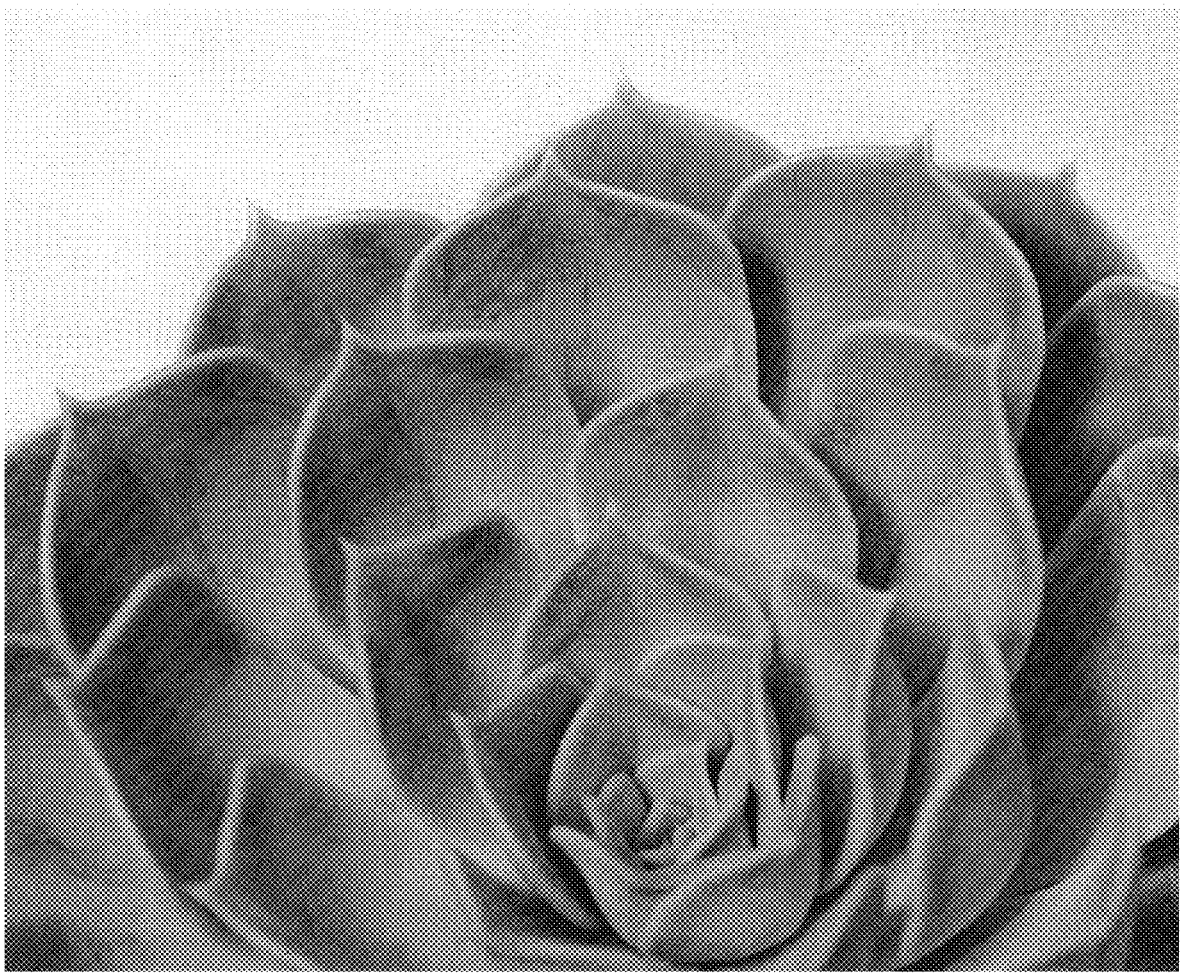
FIG. 2 illustrates, as nearly true as it is reasonably possible to make the same in color photographs of this type, the adaxial surface of the mature foliage 'OVPEARLS06'.
Figure 3:
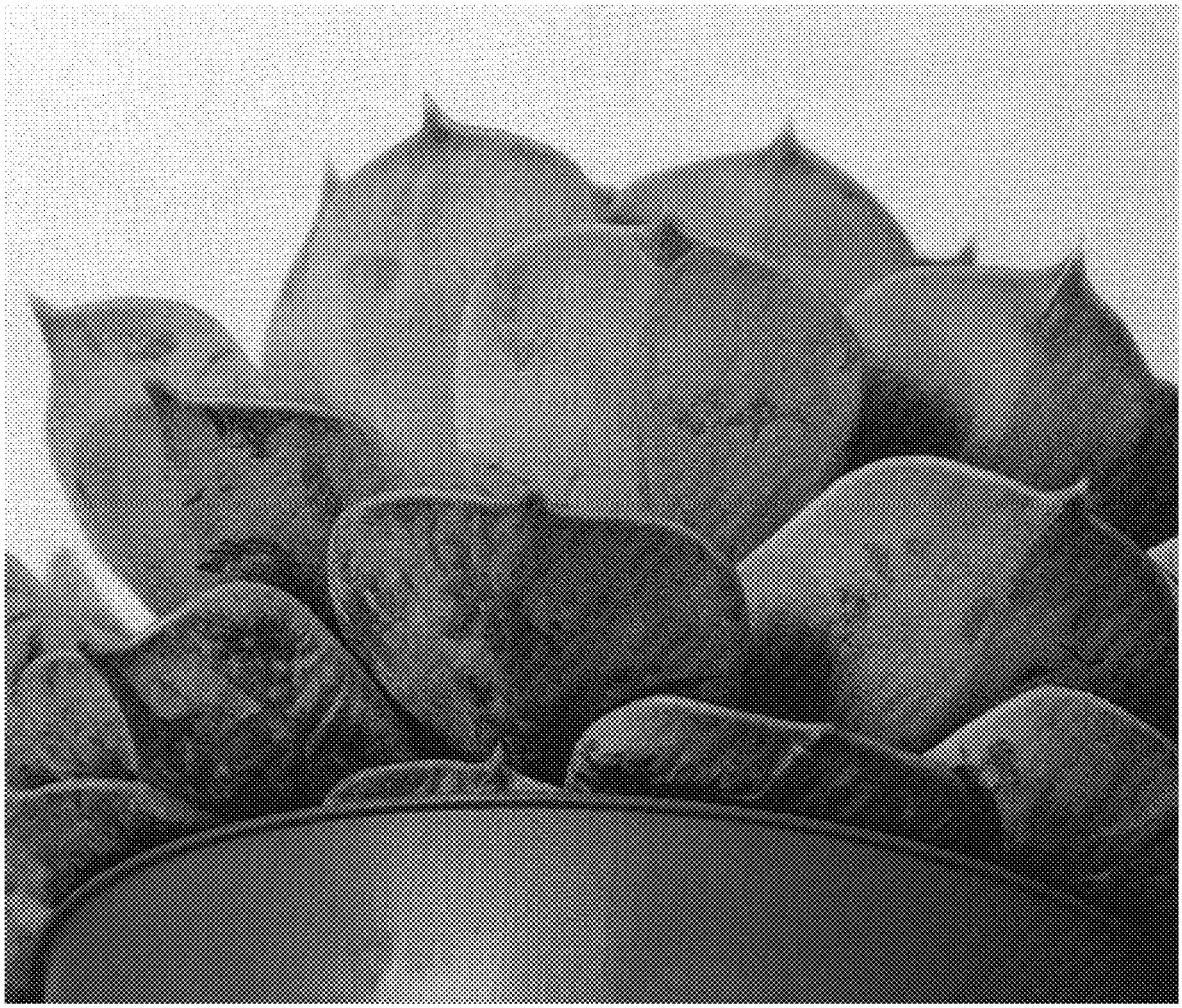
FIG. 3 illustrates, as nearly true as it is reasonably possible to make the same in color photographs of this type, the abaxial surface of the mature foliage 'OVPEARLS06'.

The following observations and measurements made in November of 2019 describe averages from a sample set of six specimens of 1 year old 'OVPEARLS06' plants grown in 12 cm nursery containers at commercial greenhouse in Bleiswijk, the Netherlands. Plants were produced using conventional greenhouse production protocols for *Echeveria* which consisted of minimal subsurface irrigation, fertilizer applications, and chemical pest control measures against thrips as required. No other chemical pest and disease control measures were taken. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'OVPEARLS06' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVPEARLS06' and a comparison with the parent and closest known comparator is provided below.

Plant description:

*Growth habit*.—Succulent perennial with foliage growing in a compact, non-branched basal rosette.

*Plant form*.—Flattened to flattened globular.

*Height from soil level to top of foliar plane*.—9.8 cm.

*Plant spread*.—Average of 18.0 cm.

*Growth rate*.—Moderately fast.

*Plant vigor*.—Moderately vigorous.

*Propagation*.—Type — Leaf cuttings. Time to initiate rooting — Approximately 5 weeks at an approximate temperature of 21 degrees Celsius. Crop time — Approximately 1 year to produce a marketable plant in a 12 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—No stems or branches; leaves arranged in a basal rosette.

Foliage:

*Arrangement*.—Rosette.

*Division*.—Simple.

*Attachment*.—Sessile.

*Quantity*.—Approximately 72 leaves per rosette.

*Shape*.—Spatulate to obovate.

*Dimensions*.—8.4 cm long, 3.9 cm wide, and 0.7 cm thick.

*Aspect*.—Slightly concave; distal portion of the leaf is curled upward at an approximate angle of 40 degrees to the proximal portion of the leaf.

*Attitude*.—Foliage is held upright and outward at and near the center of the rosette and becomes progressively more relaxed towards the outer whorls of foliage.

*Apex*.—Bluntly apiculate.

*Base*.—Cuneate.

*Margin*.—Entire; not undulated.

*Pubescence, texture and luster of the adaxial surface*.—Glabrous, smooth, and glaucescent.

*Pubescence, texture and luster of the abaxial surface*.—Glabrous, smooth, and glaucescent.

*Color*.—Juvenile foliage, adaxial surface — Greyed-green, nearest to RHS 191B; fading to grey towards the apex, nearest to in between RHS 201A and 201B; fading to greyed-green towards the base, nearest to RHS 194A; base is purple, nearest to RHS 75D; narrowly margined greyed-green, nearest to RHS 190C, and lightly suffused with white towards the apex, nearest to RHS N155C. Leaves are covered with a thin layer of epicuticular wax which is colored black, nearest to in between RHS 202C and 202D. Juvenile foliage, abaxial surface — Greyed-green, nearest to RHS 194B; darker towards the apex; nearest to RHS 191A; base is purple, nearest to RHS 75D; narrowly margined greyed-green, nearest to RHS 190D, and lightly suffused with greyed-red towards the apex, nearest to RHS N182D. Leaves are covered with a thin layer of epicuticular wax which is colored black, nearest to RHS 202C. Mature foliage, adaxial surface — Greyed-green, nearest to RHS 197B; darker towards the apex; nearest to RHS 197A; lighter towards the base, nearest to RHS 196A; narrowly margined purple, nearest to RHS 75D, and fading to greyed-green near the apex, nearest to in between RHS 195B and 195C. Leaves are covered with a thin layer of epicuticular wax which is colored black, nearest to in between RHS 202C and 202D. Mature foliage, abaxial surface — Greyed-green, nearest to RHS 197B; transitioning to brown towards the apex; nearest to RHS N200B; fading lighter towards the base, nearest to RHS 196A; narrowly margined purple, nearest to RHS 75D, and fading to greyed-green near the apex, nearest to RHS 195B. Leaves are covered with a thin layer of epicuticular wax which is colored black, nearest to RHS 202C.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

COMPARISONS WITH THE PARENT PLANT

Plants of the new cultivar 'OVPEARLS06' differ from the parent, an unnamed *Echeveria lilacina* plant (not patented) in the following characteristics described in Table 1 below.

TABLE 1

| Characteristic | 'OVPEARLS06' | The parent. |
|---|---|---|
| Foliage attitude. | Foliage is more upright. | Foliage is less upright. |
| Foliage apex. | Bluntly apiculate. | Long apiculate. |

TABLE 1-continued

| Characteristic | 'OVPEARLS06' | The parent. |
|---|---|---|
| General coloration of the foliage, epicuticular wax removed. | Darker shade of greyed-green. | Lighter shade of greyed-green. |

COMPARISONS WITH THE CLOSEST KNOWN COMPARATOR

Plants of the new cultivar 'OVPEARLS06' differ from *Echeveria* 'OVPEARLS02' (U.S. Plant Pat. No. 30,197), which is the closest known comparator, in the following characteristics described in Table 2 below.

TABLE 2

| Characteristic | 'OVPEARLS06' | 'OVPEARLS02' |
|---|---|---|
| Foliage attitude. | Foliage is more upright. | Foliage is more relaxed. |
| General coloration of the foliage. | Gray. | Light blue-gray with a light pink hue towards the apex. |
| General coloration of the foliage margins. | Pale pink and fading to white at the apex. | Darker pink, particularly at the apex. |

That which is claimed is:

1. A new and distinct variety of *Echeveria* plant named 'OVPEARLS06', substantially as described and illustrated herein.

* * * * *